United States Patent [19] [11] 4,062,854
Grushkin [45] Dec. 13, 1977

[54] PROCESS FOR PREPARING N-SUBSTITUTED-8,13-DIOXODINAPHTHO-(2,1-b; 2',3'-d)FURAN-6-CARBOXAMIDES

[75] Inventor: Bernard Grushkin, Pittsford, N.Y.

[73] Assignee: Xerox Corporation, Stamford, Conn.

[21] Appl. No.: 377,667

[22] Filed: July 9, 1973

[51] Int. Cl.$^2$ .............................................. C07D 307/92

[52] U.S. Cl. ............................ 260/295 A; 260/250 A; 260/250 B; 260/256.4 R; 260/294.8 A; 260/294.8 C; 260/294.9; 260/295 K; 260/295.5 P; 260/295.5 B; 544/208; 544/209; 544/211; 544/212

[58] Field of Search ......... 260/294.9, 295 A, 295.5 P, 260/294.8 A, 249.5, 256.4 R; 96/1.2

[56] References Cited

U.S. PATENT DOCUMENTS 3,447,922 6/1969 Weinberger ........................ 96/1.2 X

OTHER PUBLICATIONS

Buu–Hoi et al., Chem. Abstracts, vol. 47 (21), 11,179h–i, (1953).

Buu–Hoi et al., J. Chem. Soc., London, pp. 4699–4700, (1952).

Raphael et al., Advances In Organic Chemistry, Methods and Results, vol. 5, Interscience Publishers, pp. 2–7, (1965).

*Primary Examiner*—Alan L. Rotman

[57] ABSTRACT

An improved method of preparing N-substituted-8,13-dioxodinaphtho-(2,1-b; 2',3'-d)-furan-6-carboxamides is provided. An acid acceptor selected from the group consisting of carbonates and bicarbonates of alkali metals, oxides of alkaline earth metals, and alkali metal and alkaline earth salts of organic acids; and a solvent selected from the group consisting of alcohols, 1-chloronaphthalene, dimethylformamide, dimethylacetamide, high boiling ethers such as bis-(2-methoxyethyl) ether and mixtures thereof are heated with 2,3-dichloro-1,4-naphthoquinone and a suitable N-substituted amide of 2-hydroxy-3-naphthoic acid. Preferably, the acid acceptor and solvent are selected so that an isolatable intermediate is formed. The intermediate is purified and then further reacted to obtain a high-purity product.

12 Claims, No Drawings

PROCESS FOR PREPARING N-SUBSTITUTED-8,13-DIOXODINAPHTHO-(2,1-B; 2',3'-D)FURAN-6-CARBOXAMIDES

This invention relates in general to new methods of preparing N-substituted-8,13-dioxodinaphtho-(2,1-b; 2',3'-d)-furan-6-carboxamides. More specifically, the present invention relates to highly economical methods for preparing high-purity compositions of this type.

The compounds prepared by the present invention have a wide range of utilities. These compounds are photoconductive and can be used in a wide variety of mono- and polychromatic imaging processes. Furthermore, these compounds can be used as pigments in any environment wherein their brilliant, intense, yellow color may be desired. Many uses for the compositions prepared by the present invention are discussed in U.S. Pat. No. 3,447,922 to Lester Weinberger. Further exemplary of the processes which can employ these compositions are the migration imaging processes as discussed in U.S. Pat. No. 3,520,681, to W.L. Goffe; U.S. Ser. No. 837,591, filed June 30, 1969, Pat. No. 4,013,462; U.S. Ser. No. 837,780, filed June 30, 1969; and U.S. Ser. No. 199,683, filed Nov. 17, 1971 now abandoned; and the manifold imaging processes as discussed in U.S. Ser. No. 708,380, filed Feb. 26, 1969, by W.G. VanDorn now U.S. Pat. No. 3,707,638; and U.S. Pat. No. 3,556,783, to Kyriakakis. These uses are merely exemplary and are not to be considered as limiting.

U.S. Pat. No. 3,447,922, referred to above, teaches that N-substituted-8,13-dioxodinaphtho-(2,1-b; 2',3'-d)-furan-6-carboxamides having the general formula (I):

(I)

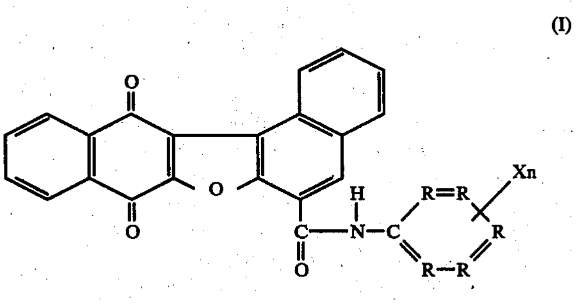

wherein:

- each R is individually selected from the group consisting of N and "CH", from 1–3 R's being N;
- each X is selected from the group consisting of H, $CH_3$, $C_2H_5$, $NO_2$, $OCH_3$, $OC_2H_5$, CN, $SO_2NH_2$, $CO_2CH_3$, $CO_2C_2H_5$, $SO_2NHC_6H_5$, Cl, F, Br, I and mixtures thereof; and
- *n* is a positive integer from 1–4;

can be prepared by reacting 2,3-dichloro-1,4-naphthoquinone, i.e., (II)

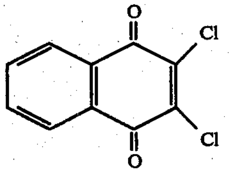

in boiling pyridine with an N-substituted amide of 2-hydroxy-3-naphthoic acid of the formula (III):

(III)

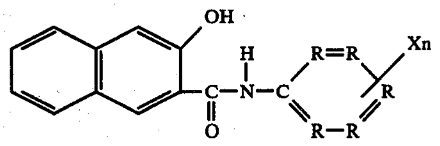

wherein R, X and *n* are as defined above.

The compounds prepared according to this reaction contain considerable amounts of impurities which greatly reduce the photosensitivity of these compounds and must, therefore, be removed. Typically, these compounds must be purified by digesting the crude product in hot pyridine and then recrystallizing the purified compound. Moreover, the pyridine used as the solvent and acid acceptor in this reaction is a very costly material. When more than small amounts of the pigment are desired, it is necessary to use an aliphatic organic base such as triethylamine and a solvent in place of the pyridine. However, the organic bases are also costly. Aliphatic bases are free of some of the disadvantages of pyridine, but still produce products which require further purification, just as those produced using pyridine.

Accordingly, it is an object of the present invention to provide an improved method for producing compounds of formula (I).

It is a further object of the present invention to provide a method for producing compounds of formula (I) of increased purity.

It is yet a further object of the present invention to provide a more economical method for producing compounds of formula (I).

These and other objects are accomplished by the process of the present invention which comprises: (a) heating (II)

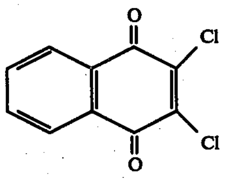

with a compound of the formula:

(III)

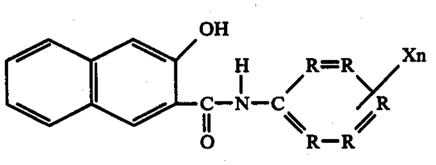

wherein R, X, and *n* are as defined in formula (I), in the presence of an inorganic acid acceptor and a solvent.

In a preferred embodiment of the present invention, the inorganic acid acceptor and the solvent are selected such that an intermediate of the following formula (IV) is produced in step (a):

(IV)

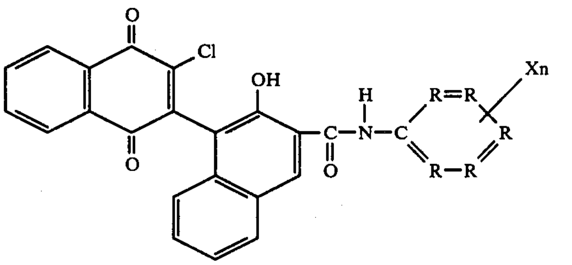

wherein R, X and *n* are as defined above.

The intermediate is separated from the reaction mixture including substantially all of the by-products of the reaction in step (a); and the intermediate is then heated in the presence of an inorganic acid acceptor and a solvent to obtain the product of the formula (I).

A wide variety of solvents and inorganic bases may be employed according to the present invention. The most critical, limiting parameter in base and solvent selection is the purity of the resultant product. The base and solvent must be so selected that the reaction does not proceed too rapidly and thereby cause occlusion of impurities. Thus, the base must be soluble enough in the solvent so that it is available to neutralize the hydrochloric acid produced by the reaction, but not so soluble as to drive the reaction at such a rate that impurities are occluded within the precipitated product.

Among the inorganic bases which are suitable to prepare the compounds of formula (I) according to the present invention are: the carbonates and bicarbonates of the alkali metals, such as sodium carbonate, sodium bicarbonate, potassium carbonate and potassium bicarbonate; oxides of the alkaline earth metals such as calcium oxide; and alkali metal and alkaline earth salts of organic acids, such as sodium acetate and calcium acetate.

Among the solvents which have been found suitable according to the present invention are: alcohols, such as ehtanol, n-propanol, i-propanol, n-butanol, i-butanol, and the like; dimethylacetamide; high boiling ethers, such as bis-(2-methoxyethyl) ether; 1-chloronaphthalene; and dimethylformamide. Additionally, combinations of these solvents may be used. For example, the use of dimethylformamide along with an alcohol or 1-chloronaphthalene will increase the reaction rate. It is noted in this regard that in some instances it is desirable to increase the reaction rate so that the product (I) is produced at an economically attractive rate; and, at other times, it is desirable to reduce the reaction rate so that a more pure product can be obtained. For example, in order to obtain a product (I) directly through the use of a bicarbonate and an alcohol solvent, it is necessary to add at least 5 vol. % of dimethylformamide, based on the volume of alcohol. And, to complete the reaction within a reasonable time, 20 to 100 vol. % of dimethylformamide is used.

A preferred solvent system comprises 1-chloronaphthalene and dimethylformamide used together. The exact ratio of the 1-chloronaphthalene to the dimethylformamide is arbitrary, however, good yields are obtained when the ratio is within the range of from about 1:2 to 2:1. Using this solvent system it is possible to obtain well developed crystals of product (I) in high purity having diameters ranging from about 50–100 microns and larger. Dimethylacetamide is also an effective solvent for obtaining larger crystals. In this case, the dimethylacetamide can be initially added to the reaction mixture, with the isopropanol or other precipitating solvent being slowly added thereto.

The reaction temperature will vary depending upon the solvent system and the base used. In general, reaction temperatures ranging from 50° C. to reflux at atmospheric pressure can be used. The preferred reaction temperature ranges for producing product (I) are indicated in Table I below for several representative base/solvent systems.

Table I

| Base | Solvent | Preferred Temperature (° C.) |
|---|---|---|
| $K_2CO_3$ or $Na_2CO_3$ | i-propanol/dimethylformamide | 55 to 100 |
| $K_2CO_3$ or $Na_2CO_3$ | Dimethylformamide | 55 to 120 |
| $K_2CO_3$ or $Na_2CO_3$ | Dimethylacetamide | 65 to 140 |
| $K_2CO_3$ or $Na_2CO_3$ | i-propanol | 65 to 84 |
| $K_2CO_3$ or $Na_2CO_3$ | Chloronaphthalene/dimethylformamide | 80 to 150 |
| $KHCO_3$ or $NaHCO_3$ | i-propanol/dimethylformamide | 75 to 100 |

When the solvent system consists of chloronaphthalene and dimethylformamide, it is desirable to carry out the reaction at a higher temperature in order to provide for the production of larger crystals of product (I).

While it is possible to produce product (I) directly from reactants (II) and (III) according to the above-described procedure, thereby eliminating the usual, subsequent purification step, the preferred method according to the present invention includes isolating and purifying an intermediate product formed during the reaction and subsequently reacting it with an inorganic base in the presence of a solvent to product product (I). According to this embodiment, the reaction is believed to follow the following course.

(II) (III)

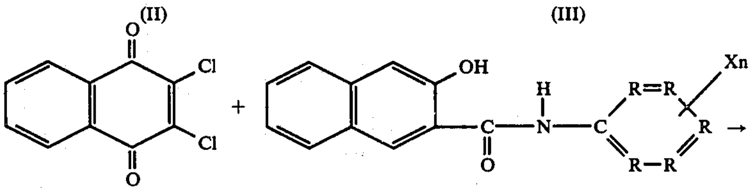

-continued (IV)

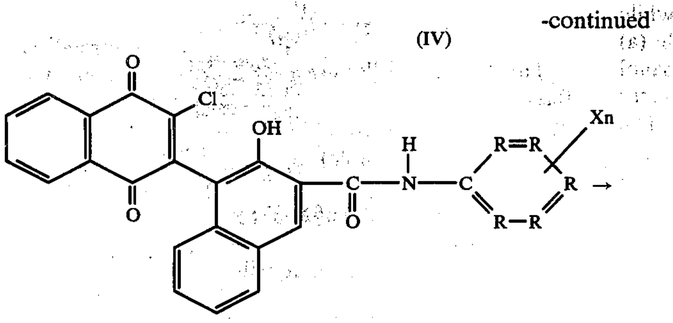

(I)

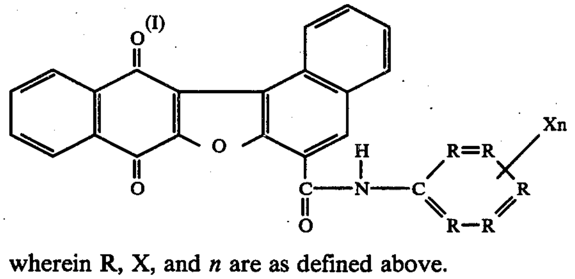

wherein R, X, and *n* are as defined above.

It has been discovered in accordance with the present invention that reactant (II) is completely converted during the course of the reaction. It was further found that the conversion of the reactant (II) results in the production of the intermediate (IV) and by-products. By isolating the intermediate (IV), and removing substantially all of the by-products and other impurities, it is possible to obtain high conversions of the intermediate (IV) to high-purity product (I).

In order to obtain the intermediate in isolatable form, it is necessary to select a base/solvent system which facilitates isolation. Among the inorganic bases which may be used according to this preferred embodiment are the alkali metal salts of weak organic acids, sodium carbonate and sodium bicarbonate. Preferred among the alkali metal salts of weak organic acids are sodium acetate and sodium acetate trihydrate.

Sodium carbonate tends to push the reaction to completion unless the reaction is interrupted before significant conversion of intermediate (IV) to product (I). The progress of the reaction can be followed by observing the color changes which occur, thus enabling the interruption of the reaction at the appropriate time for removal of the intermediate (IV). For example, the reaction mixture undergoes a series of color changes, generally from deep green to olive, then to yellow, and finally to yellow-orange. The olive color indicates the presence of the intermediate without substantial conversion thereof to the product (I). The solvents useful for the preferred embodiment which involve the isolation of the intermediate (IV) include alcohols, particularly those having from two to four carbon atoms, with isopropanol being the most preferred.

Reactants (II) and (III) may be present in any effective relative amounts, with the exact portions being dictated primarily by economics. Preferably, the ratio of reactant (II) to reactant (III) ranges from about 2:3 to 3:2, with the most preferred ratio providing a small excess of the dichloronaphthoquinone. The solvent is preferably present in an amount of about 2 liters per mole of reactants, but again, the exact amount is dependent upon the particular solvent/base system and is largely determined by the economics. Likewise, the amount of the inorganic base required is not critical, but can be varied over a wide range depending upon the particular processing scheme and the economics thereof. Preferably, the inorganic base is present in an amount which yields at least about two equivalents for the embodiment wherein the product (I) is formed directly, and about one equivalent in the preferred embodiment wherein the intermediate (IV) is to be isolated.

In order to isolate and remove substantially all of the impurities from the intermediate, the reaction mixture is rapidly brought to reflux and maintained there until the deep green-to-olive coloration is observed. At this point the reaction mixture is filtered while hot to yield the intermediate as a red solid precipitate. The precipitate is washed thoroughly with a suitable liquid which removes the impurities but does not substantially dissolve the precipitate. Examplary of suitable liquids are: alcohols such as i-propanol, methanol and ethanol; ketones such as acetone, methylethyl ketone and methylisobutyl ketone; aromatic solvents such as hot chlorobenzene; or hot orthodichlorobenzene; or ethers such as dioxane or tetrahydrofuran. Acetone and lower alcohols such as i-propanol are preferred. The intermediate is then admixed with any suitable solvent/base system, such as those described above for the direct preparation of product (I), and heated to reaction temperature for sufficient time to obtain substantially quantitative conversion of the intermediate (IV) to the product (I).

The following examples are presented for the sole purpose of further illustrating the present invention and are not to be taken as limiting in any sense. Unless otherwise indicated all parts and percentages are by weight.

EXAMPLE I

The following materials are added to a three-liter flask, fitted with a mechanical stirrer, thermometer, and an efficient condenser:

0.1 mole of 2,3-dichloro-1,4-naphthoquinone,
0.1 mole of N-2'-pyridyl-2-hydroxyl-3-naphthamide,
0.3 mole of anhydrous powdered sodium carbonate, and
2 liters of isopropanol.

The resultant slurry is brought to reflux and maintained there until the slurry becomes a yellow-orange in color. This occurs in about 1.5 hours. The solids are then removed from the reaction mixture by filtering while hot. The solids are then washed successively with: (a) 300 milliliters of dimethylformamide, (b) isopropanol until the wash is no longer yellow, (c) deionized water until negative to chloride ion, and (d) isopropanol. The washed solid pigment is then air dried to yield about 81%, based on 2,3-dichloro-1,4-naphthoquinone, of a yellow-orange pigment having the formula:

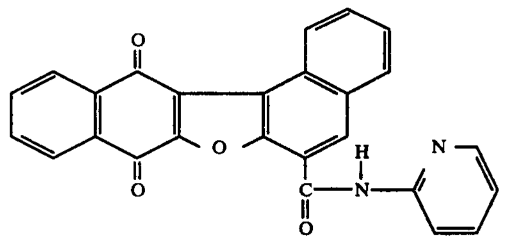

EXAMPLE II

The following materials are added to a three-liter flask fitted with a mechanical stirrer, a thermometer and an efficient condenser:

0.05 mole of 2,3-dichloro-1,4-naphthoquinone,
0.05 mole of N-2'-pyridyl-2-hydroxyl-3-naphthamide,
0.40 mole of anhydrous sodium carbonate, and
200 milliliters of 1-chloronaphthalene.

This reaction mixture is heated to 140° C. and 400 milliliters of dimethylformamide are slowly added to the reaction mixture over a period of 1 hour. The reaction mixture is maintained at 140° C. for an additional 2 hours, after which time 100 milliliters of isopropanol are added while slowly cooling the reaction mixture over a period of 1 hour to a temperature of 60° C. The solids are separated from the cooled reaction mixture by filtration. The solids are then washed successively with: (a) two, 200 milliliter portions of dimethylformamide, (b) isopropanol until the wash is no longer yellow, (c) deionized water until negative to chloride ion, (d) 200 milliliters of dimethylformamide, and (e) isopropanol. The resultant solid is then air dried to yield about 76% of a yellow-orange pigment having the same structure as the product obtained in Example I.

EXAMPLE III

The following materials are added to a three-liter flask fitted with a mechanical stirrer, a thermometer and an efficient condenser:

0.05 mole of 2,3-dichloro-1,4-naphthoquinone,
0.05 mole of N-2'-pyridyl-2-hydroxyl-3-naphthamide,
0.2 mole of sodium carbonate, and
400 milliliters of dimethylacetamide.

The resultant mixture is then heated to 140° C. and maintained there for a period of 1 hour after which time 200 milliliters of isopropanol are slowly added to the mixture over a 1 hour period. The reaction temperature is then lowered to 50° C. and the solids are separated from the reaction mixture by filtration. The solids are then washed at room temperature with successive portions of: (a) 100 milliliters of dimethylformamide, (b) isopropanol until the wash was no longer yellow, (c) deionized water until negative to chloride ion, and (d) isopropanol. The resultant solid was then dried to yield 15 grams of a yellow-orange pigment having the same structure as the product of Example I for an overall yield of 75%.

EXAMPLE IV

The following materials are added to a three-liter flask fitted with a mechanical stirrer, a thermometer and an efficient condenser:

127 g. (0.56 mole) of 2,3-dichloro-1,4-naphthoquinone,
132 g. (0.50 mole) of N-2'-pyridyl-2-hydroxyl-3-naphthamide,
80 g. of sodium acetate trihydrate, and
2 liters of isopropanol.

The reaction mixture is heated at reflux for 3 hours to obtain a green-to-olive color, and then filtered hot to remove the solids. The solids are then washed with successive portions of: (a) 2 liters of isorpopanol, (b) 2 liters of deionized water, and (c) 1 liter of isopropanol. The washed solid is then dried to yield 180 g. of a red solid melting at from 239°-250° C. The overall yield on the basis of the 2,3-dichloro-1,4-naphthoquinone is found to be 79.5%. This solid is an intermediate product defined by the following structural formula:

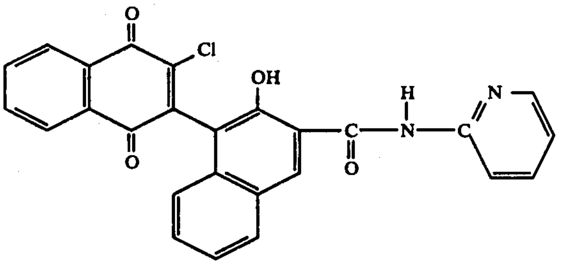

EXAMPLE V

To prepare the desired pigment product from the intermediate prepared in Example IV, the following materials are added to a reaction vessel:

9.1 g. (0.02 mole) of the intermediate,
3.05 g. (0.022 mole) of potassium carbonate, and
200 milliliters of dimethylformamide.

The resultant reaction mixture is nearly black at room temperature. The reaction mixture is heated for 15 minutes. Upon heating, the color of the reaction mixture gradually changes from olive to yellow, and finally to yellow-orange. The reaction mixture is then cooled slowly before removing the solids by filtering at room temperature. The filtered solids are washed with isopropanol and air dried to yield 8.28 g. of a crystalline yellow-orange solid melting at 332°-334° C. The yield of the recovered solid, based on the weight of the intermediate, is 99%. This product has the same structure as the product of Example I.

EXAMPLE VI

To produce the desired yellow-orange pigment from the intermediate produced in Example IV, a reaction mixture is prepared by adding 0.1 mole of the intermediate over a period of 1 hour to a reaction vessel containing 0.30 mole of sodium carbonate and 2.5 liters of dimethylformamide maintained at 95° C. The resultant slurry is maintained at 95° C. for 3 hours after the addition of the intermediate is complete, and is then cooled at 60° C. and filtered to recover the solids. The solids are washed with isopropanol and air dried to yield 36.8 g. of a yellow-orange solid melting at 327°-330° C. The yield of the yellow-orange pigment of Example I, based upon the weight of the intermediate, is found to be 88%.

EXAMPLE VII

The following materials are added to a three-liter flask fitted with a mechanical stirrer, a thermometer, and an efficient condenser:

1 liter of isopropanol,
45.4 g. (0.02 mole) of 2,3-dichloro-1,4-naphthoquinone,
52.8 g. (0.02 ole) of N-2'-pyridyl-2-hydroxyl-3-naphthamide, and
23.3 g. of sodium carbonate.

This reaction mixture is rapidly brought to reflux, maintained there for 1.5 hours and then filtered while hot to separate the red solid intermediate. This intermediate has the same structural formula as that obtained in Example IV. The intermediate is then washed with three, 200 milliliter aliquots of isopropanol. The thus washed intermediate is then returned to the empty reaction flask along with 2 liters of isopropanol to produce a reaction slurry. The reaction slurry is brought to reflux and 500 milliliters of dimethylformamide are added within 5 minutes. After 1 hour of reflux, isopropanol is removed by distillation until the final solvent mixture contains approximately 500 milliliters of isopropanol and 500 milliliters of dimethylformamide. The reaction mixture is then allowed to cool to 60° C. and filtered at that temperature. The resultant precipitate is washed successively with portions of: (a) isopropanol, (b) deionized water, and (c) isopropanol. The precipitate is then air dried to yield 68.0 g. of yellow-orange pigment melting at 328°-333° C. The overall yield of this procedure is 81.2%, based on the weight of the 2,3-dichloro-1,4-naphthoquinone. The pigment has the same structural formula as the product of Example I.

Other modifications of the present invention will occur to those skilled in the art upon reading and present disclosure. All of the modifications are intended to be included within the scope of the present invention which is limited only by the following claims.

What is claimed is:

1. A method of preparing a compound of the formula:

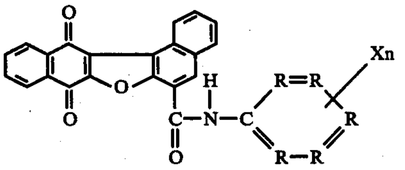

wherein:

each R is selected from the group consisting of N and "CH", from 1-3 R's being N;

each X is selected from the group consisting of H, $CH_3$, $C_2H_5$, $NO_2$, $OCH_3$, $OC_2H_5$, CN, $SO_2NH_2$, $CO_2CH_3$, $CO_2C_2H_5$, $SO_2NHC_6H_5$, Cl, F, Br, I and mixtures thereof; and

*n* is a positive integer from 1-4;

which comprises heating to a temperature within the range of from 50° C. to reflux a reaction mixture comprising:

i. 2,3-dichloro-1,4-naphthoquinone, ii. a compound of the formula:

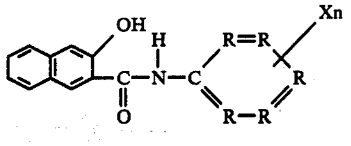

wherein R, X, and *n* are as defined above, iii. an inorganic base selected from the group consisting of carbonates and bicarbonates of the alkali metals, oxides of the alkaline earth metals, and alkali metal and alkaline earth salts of organic acids; and iv. a solvent selected from the group consisting of alcohols, 1-chloronaphthalene, high boiling ethers, dimethylformamide, dimethylacetamide and mixtures thereof.

2. A method according to claim 1 wherein the base is a member selected from the group consisting of $Na_2CO_3$, $NaHCO_3$, $K_2CO_3$, $KHCO_3$, CaO and sodium acetate.

3. A method according to claim 2 wherein the solvent comprises isopropanol.

4. A method according to claim 2 wherein the solvent comprises dimethylacetamide.

5. A method according to claim 2 wherein the solvent comprises dimethylformamide.

6. A method according to claim 5 wherein the solvent additionally comprises i-propanol.

7. A method according to claim 5 wherein the solvent additionally comprises 1-chloronaphthalene.

8. A method of preparing compounds of the formula:

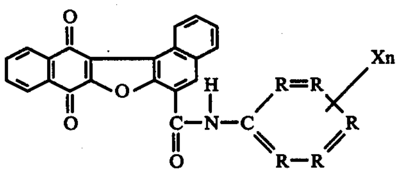

wherein:

each R is selected from the group consisting of N and C, from 1-3 R's being N;

each X is selected from the group consisting of H, $CH_3$, $C_2H_5$, $NO_2$, $OCH_3$, $OC_2H_5$, CN, $SO_2NH_2$, $CO_2CH_3$, $CO_2C_2H_5$, $SO_2NHC_6H_5$, Cl, F, Br, I and mixtures thereof; and

*n* is a positive integer from 1-4; which comprises:

a. heating at a temperature of from 50° C. to reflux a reaction mixture comprising:

i. 2,3-dichloro-1,4-naphthoquinone, ii. a compound of the formula:

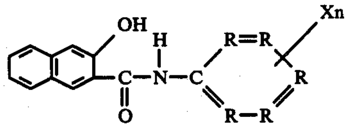

wherein R, X and *n* are as defined above, iii. an inorganic base selected from the group consisting of alkali metal salts of weak organic acids, sodium carbonate and sodium bicarbonate, and iv. a solvent selected from the group consisting of alcohols, to thereby form an intermediate of the formula:

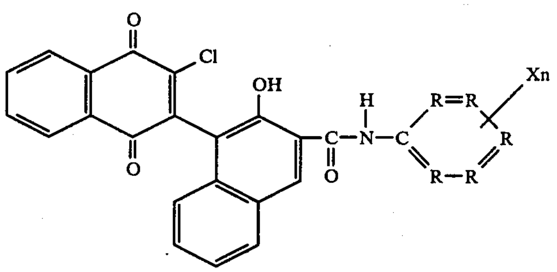

wherein R, X, and *n* are as defined above;

b. separating the intermediate from the reaction mixture and removing therefrom any by-products produced during the reaction of step (a);

c. admixing the intermediate with an inorganic base and a solvent for the base; and d. heating the mixture produced in step (c).

9. A method according to claim 8 wherein the solvent in step (a) is an alcohol having from 2 to 4 carbon atoms.

10. A method according to claim 9 wherein the solvent in step (a) comprises i-propanol.

11. A method according to claim 9 wherein the base in step (a) comprises sodium acetate.

12. A method according to claim 9 wherein the base in step (a) comprises $Na_2CH_3$.

* * * * *